(12) United States Patent
Woodson et al.

(10) Patent No.: US 11,911,010 B2
(45) Date of Patent: Feb. 27, 2024

(54) MEDICAL INSTRUMENT PORT FOR USE WITH PROTECTIVE FACE COVERINGS

(71) Applicant: THE MEDICAL COLLEGE OF WISCONSIN, INC., Milwaukee, WI (US)

(72) Inventors: B. Tucker Woodson, Milwaukee, WI (US); David M. Poetker, Brookfield, WI (US); Guilherme Garcia, Milwaukee, WI (US); Bonnie Patricia Freudinger, Greenfield, WI (US); David R. Friedland, Milwaukee, WI (US); Todd A. Loehrl, Delafield, WI (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 65 days.

(21) Appl. No.: 17/308,537

(22) Filed: May 5, 2021

(65) Prior Publication Data

US 2021/0346668 A1 Nov. 11, 2021

Related U.S. Application Data

(60) Provisional application No. 63/054,639, filed on Jul. 21, 2020, provisional application No. 63/020,217, filed on May 5, 2020.

(51) Int. Cl.
*A61M 39/04* (2006.01)
*A61B 1/00* (2006.01)
*A61B 1/233* (2006.01)
*A41D 13/11* (2006.01)
*A61B 90/00* (2016.01)

(52) U.S. Cl.
CPC ............ *A61B 1/233* (2013.01); *A41D 13/11* (2013.01); *A61B 1/00147* (2013.01); *A61B 90/05* (2016.02); *A61M 39/04* (2013.01)

(58) Field of Classification Search
CPC ..... A61B 1/233; A61B 1/00147; A61B 90/05; A61B 1/00154; A41D 13/11; A61M 39/04
See application file for complete search history.

(56) References Cited

U.S. PATENT DOCUMENTS

| 4,197,848 | A | * | 4/1980 | Garrett | A61F 5/4404 604/326 |
| 4,436,519 | A | * | 3/1984 | O'Neill | A61M 39/04 137/847 |

(Continued)

OTHER PUBLICATIONS

Workman, A.D. et al., Endonasal instrumentation and aerosolization risk in the era of COVID-19: simulation, literature review, and proposed mitigation strategies, International Forum of Allergy & Rhinology, vol. 10, No. 7, Jul. 2020, pp. 798-805.

*Primary Examiner* — Theodore J Stigell
(74) *Attorney, Agent, or Firm* — Quarles & Brady LLP

(57) ABSTRACT

A medical instrument port is described for use with a surgical mask or other protective face covering. The medical instrument port provides a sealed pathway through which a medical instrument can be passed without exposing the clinician to aerosolized droplets expelled from the patient's respiratory system when the medical instrument is introduced into the patient's nasal and/or oral passages.

21 Claims, 6 Drawing Sheets

(56) References Cited

U.S. PATENT DOCUMENTS

| | | | | |
|---|---|---|---|---|
| 5,147,336 A * | 9/1992 | Wendell | ............ | A61M 39/0613 |
| | | | | 604/533 |
| 5,431,158 A * | 7/1995 | Tirotta | .............. | A61M 16/0488 |
| | | | | 128/207.14 |
| 5,465,712 A * | 11/1995 | Malis | .................... | A61M 16/06 |
| | | | | 128/912 |
| 6,165,168 A * | 12/2000 | Russo | ................. | A61M 39/045 |
| | | | | 604/533 |
| 8,365,734 B1 * | 2/2013 | Lehman | ................. | A61B 5/097 |
| | | | | 128/206.28 |
| 11,000,655 B1 * | 5/2021 | Fox | ................... | A61M 16/0616 |
| 11,524,152 B1 * | 12/2022 | Leeflang | ........... | A61M 25/0097 |
| 2010/0280456 A1 * | 11/2010 | Nijland | ................. | A61M 39/06 |
| | | | | 604/167.03 |
| 2021/0298383 A1 * | 9/2021 | Donzelli | .............. | A62B 23/025 |
| 2021/0345699 A1 * | 11/2021 | Bush | .................. | A41D 13/1146 |
| 2023/0110218 A1 * | 4/2023 | Hafeman | ........... | B05B 17/0646 |
| | | | | 128/203.14 |

* cited by examiner

MEDICAL INSTRUMENT PORT FOR USE WITH PROTECTIVE FACE COVERINGS

CROSS-REFERENCE TO RELATED APPLICATIONS

This application claims the benefit of U.S. Provisional Patent Application Ser. No. 63/020,217, filed on May 5, 2020, and entitled "MEDICAL INSTRUMENT PORT FOR USE WITH PROTECTIVE FACE COVERINGS," and claims the benefit of U.S. Provisional Patent Application Ser. No. 63/054,639, filed on Jul. 21, 2020, and entitled "MEDICAL INSTRUMENT PORT FOR USE WITH PROTECTIVE FACE COVERINGS," each of which are herein incorporated by reference in their entirety.

BACKGROUND

Many diseases, such as the recent novel coronavirus (SARS-CoV-2) that causes COVID-19, can be transmitted by aerosolized droplets that are expelled from the respiratory system through speech, coughing, and sneezing. Clinicians and other healthcare workers are at a particular risk of being exposed to such aerosolized droplets when delivering care to infected individuals. Otolaryngologists are at a particular risk when performing procedures, such as endoscopy, where introducing a medical instrument into the nasal and/or oral passage of a patient will often cause the patient to sneeze or otherwise expel aerosolized droplets.

Personal protective equipment ("PPE"), such as surgical masks or other face coverings, can be used to reduce droplet transmission of diseases. PPE can be provided to a patient to reduce droplet transmission, but when a procedure requiring the introduction of a medical instrument, such as an endoscope, is performed on that patient the PPE needs to be removed, thereby exposing the clinician to any aerosolization from the patient during the procedure. There is a need, then, for PPE that enables a clinician to introduce a medical instrument into the nasal and/or oral passage of a patient without removing the protective barrier provided by PPE.

SUMMARY OF THE DISCLOSURE

The present disclosure addresses the aforementioned drawbacks by providing a medical instrument port that includes a first component and a second component. The first component extends from an outward facing surface to an inward facing surface and has formed therein an aperture that extends from the outward facing surface to the inward facing surface. The second component includes a flange and a tube. The flange extends from an outward facing surface to an inward facing surface, and the tube is coupled to the flange and extends from the inward facing surface of the flange to a leading edge of the tube. A central lumen is formed in the second component, which extends from the outward facing surface of the flange to the leading edge of the tube. The aperture formed in the first component is sized to receive the tube of the second component such that when in a coupled state the first component and the second component define a port through which a medical instrument can pass.

It is another aspect of the present disclosure to provide a personal protective equipment kit that includes a face mask and a medical instrument port. The medical instrument port includes a first component and a second component. The first component extends from an outward facing surface to an inward facing surface and has formed therein an aperture that extends from the outward facing surface to the inward facing surface. The second component includes a flange and a tube. The flange extends from an outward facing surface to an inward facing surface, and the tube is coupled to the flange and extends from the inward facing surface of the flange to a leading edge of the tube. A central lumen is formed in the second component, which extends from the outward facing surface of the flange to the leading edge of the tube. The aperture formed in the first component is sized to receive the tube of the second component such that when in a coupled state the first component and the second component define a port through which a medical instrument can pass. When the medical instrument port is in the coupled state the face mask is arranged between and retained by the inward facing surface of the first component and the inward facing surface of the flange.

It is yet another aspect of the present disclosure to provide a personal protective equipment kit that includes a face mask and a medical instrument port. The medical instrument port includes a mounting assembly and a seal. The mounting assembly is coupled to the face mask and has a central lumen extending therethrough to provide a pathway from a first side of the face mask to a second side of the face mask. The seal is coupled to and spans the central lumen of the mounting assembly.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here is a medical instrument port for use with a surgical mask or other similar face mask, protective covering, or fabric. The medical instrument port provides a sealed pathway through which a medical instrument can be passed without exposing the clinician to aerosolized droplets expelled from the patient's respiratory system when the medical instrument is introduced into the patient's nasal passage or mouth.

Figure 1:
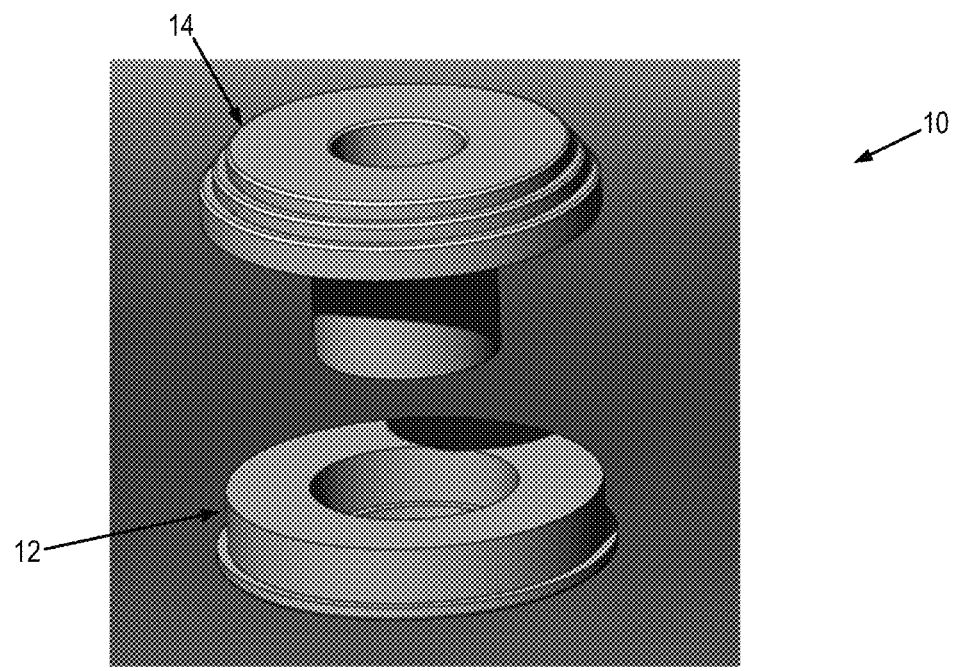
FIG. 1 shows an example medical instrument port according to some embodiments described in the present disclosure.
Figure 2:
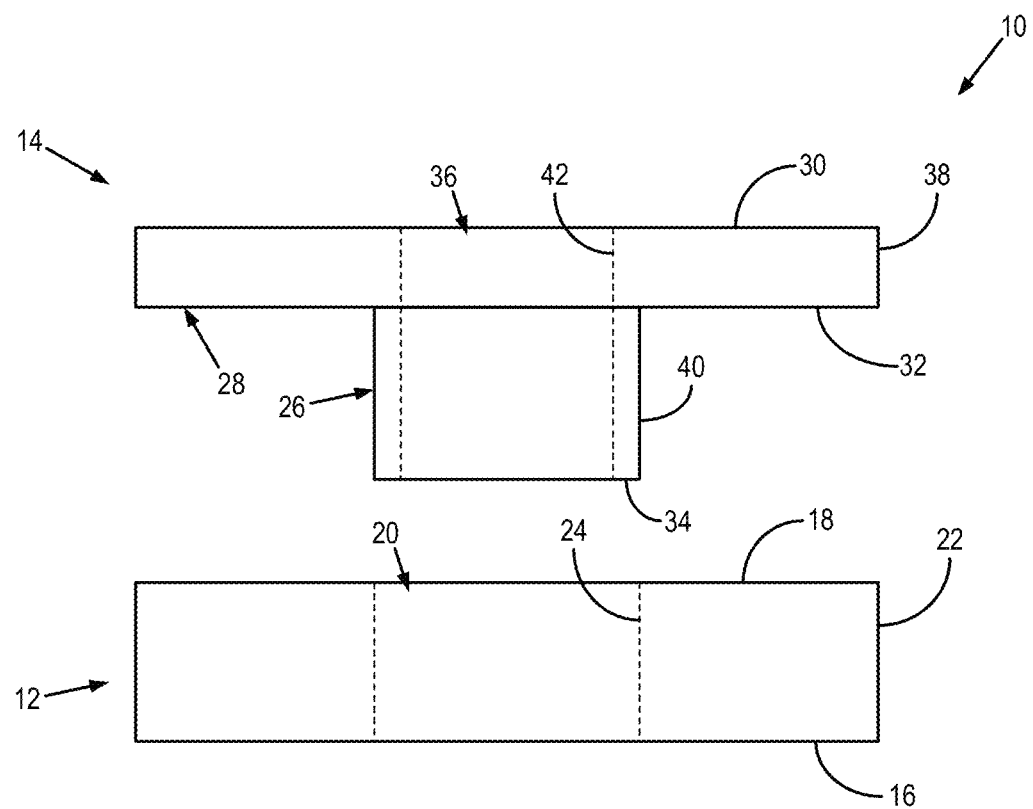
FIG. 2 shows another view of an example medical instrument port according to some embodiments described in the present disclosure.

As shown in FIGS. 1 and 2, a medical instrument port 10 according to some embodiments includes a first component 12 and a second component 14 that when mated or otherwise coupled with the first component 12 provides a pathway through which a medical instrument (e.g., an endoscope, a bronchoscope) may pass. In some configurations, the first component 12 may be a female component and the second component 14 may be a male component. In other configurations, the first component 12 and the second component 14 can be interlocking components. As will be described in more detail below, collectively, the first component 12 and the second component 14 can define a mounting assembly to hold one or more seals that prevent exposing the clinician to aerosolized droplets expelled from the patient's respiratory system when a medical instrument is introduced into the patient's nasal passage or mouth.

The first component 12 extends from an outward facing surface 16 to an inward facing surface 18 along an axis (e.g., a longitudinal axis). A central lumen 20, or aperture, extends through the first component 12 from the outward facing surface 16 to the inward facing surface 18. The outer extent of the first component 12 is defined by an outer edge 22, and the central lumen 20 is defined by an inner edge 24 of the first component 12.

In some embodiments, the first component 12 has a circular annular shape. In these instances, the outer edge 22 is defined by an outer diameter and the inner edge 24 is defined by an inner diameter. In other instances, the first component 12 can have other shapes (e.g., other polygonal shapes), and may also be arbitrarily shaped. The outer edge 22 can also define a different shape than the inner edge 24. For example, the outer edge 22 may define a square shape while the inner edge 24 may define a circular shape.

The second component 14 includes a central tube 26 and a flange 28 that is arranged at one end of the tube 26. Preferably, the tube 26 and the flange 28 are integral with each other. Alternatively, the tube 26 can be a separate component from the flange 28.

The flange 28 extends from an outward facing surface 30 to an inward facing surface 32. The tube 26 extends outward from the inward facing surface 32 of the flange 28 and terminates at a leading edge 34. A central lumen 36, or aperture, extends through the first component 12 from the outward facing surface 30 to the leading edge 34 of the tube 26. The outer extent of the flange 28 is defined by an outer edge 38, the outer extent of the tube 26 is define by an outer surface 40, and the central lumen 36 is defined by an inner surface 42 of the second component 14.

The distance between the outer surface 40 of the tube 26 and the outer edge 38 of the flange 26 define an overlap surface area on the inward facing surface 32 of the flange 26. This overlap surface area is preferably sized to be large enough to securely retain a face mask or other protective covering between the first component 12 and the second component 14 when in their coupled state.

The leading edge 34 can have a flat surface that is parallel to the inward facing surface 32 of the flange 28. Alternatively, the leading edge 34 can be angled relative to the inward facing surface 32 of the flange 28. In such instances, the leading edge 34 can define a bevel or cutting edge that facilitates piercing, puncturing, or otherwise passing the second component 14 through a face mask or other protective covering.

In some embodiments, the second component 14 has a circular annular shape. In these instances, the outer edge 38 of the flange 28 is defined by an outer flange diameter, the outer surface 40 of the tube 26 is define by an outer tube diameter, and the inner surface 42 of the central lumen 36 is defined by an inner tube diameter. In other instances, the tube 26 and/or the flange 28 of the second component 14 can have other shapes, (e.g., other polygonal shapes), and may also be arbitrarily shaped.

The central lumen 20 of the first component 12 is sized and shaped to receive the tube 26 of the second component 14. For example, the outer tube diameter can be smaller than the inner diameter of the central lumen 20 in the first component 12. In this way, the first component 12 and the second component 14 can be mated or otherwise coupled by aligning the tube 26 with the central lumen 20 of the first component 12 and then bringing the inward facing surface 18 of the first component 12 into contact with the inward facing surface 32 of the second component 14.

In some instances, the inward facing surface 18 of the first component 12 and the inward facing surface 32 of the second component 14 can be flat surfaces. In some other instances, the respective surfaces can be sized and/or shaped such that one surface can be received and retained by the other to further secure a face mask therebetween. For example, a ridge can be formed on the circumference of the inward facing surface 32 of the second component 14 and the inward facing surface 18 of the first component 12 can be sized such that it will be received within this ridge.

As one example, the first component 12 and the second component 14 can be coupled via an interference fit. As another example, the first component 12 and the second component 14 can be coupled via one or more ridges formed on the outer surface 40 of the tube 26 that are received by one or more recesses formed in the inner edge 24 of the central lumen 20 of the first component 12. In these instances, the first component 12 and the second component 14 can be snapped together.

As still another example, the first component 12 and the second component 14 can be coupled via a snap-in connection. For instance, one or more tabs can extend from the inward facing surface 32 of the second component 14 (or the inward facing surface 18 of the first component 12), each having a corresponding slot formed in the inward facing surface 18 of the first component 12 (or the inward facing surface 32 of the second component 14). In this arrangement, when the respective inward facing surfaces of the first component 12 and the second component 14 are pressed together the one or more tabs will engage with the corresponding slot(s), thereby coupling the first component 12 and the second component 14 together. Advantageously, this configuration provides additional securing of the medical instrument port 10 to the face mask or other protective covering.

The length of the tube 26 is preferably equal to the length of the central lumen 20 of the first component 12, such that when the first component 12 and the second component 14 are coupled the tube 26 does not extend beyond the outward facing surface 16 of the first component 12. Alternatively, the length of the tube 26 can be less than the length of the central lumen 20 of the first component 12.

The inner surface 42 that defines the central lumen 36 of the second component 14 is sized to receive a medical instrument, such as an endoscope, a bronchoscope, or other such medical instruments that may be provided to a patient's nasal passage and/or mouth (e.g., for delivery to the patient's trachea, bronchus, esophagus). Thus, in some examples, the central lumen 36 can have an inner diameter large enough to receive an endoscope, which may have an outer diameter in a range of 2-4 mm. As another example, the central lumen 36 can have an inner diameter large enough to receive a flexible scope for examining the tonsils, which may have an outer diameter on the order of 3 mm. In still other examples, the central lumen 36 can have an inner diameter that is large enough to receive a bronchoscope, which may have an outer diameter in a range of 2-12 mm.

The first component 12 and the second component 14 can be composed of a material such as metal, plastic, or the like. In general, the medical instrument port 10 can be designed such that it can be manufactured rapidly and inexpensively. In these instances, the first component 12 and the second component 14 are preferably made of a plastic or other polymer material, such as nylon, polyvinyl chloride ("PVC"), polystyrene, silicone, rubber, polyamide, acrylic, polyethylene or high-density polyethylene ("HDPE"), polypropylene, polysulfone, polyethylene terephthalate ("PET"), polyethylene terephthalate glycol ("PETG"), polytetrafluoroethylene ("PTFE"), polyether ether keytone ("PEEK"), polyether block amide (e.g., PEBAX), polycarbonate, acrylonitrile butadiene styrene ("ABS"), polylactic acid ("PLA"), and so on. In some instances, the first component 12 and the second component 14 can be manufactured using an injection molding technique. As another example, the first component 12 and the second component 14 can be manufactured using an additive manufacturing process, such as 3D printing.

Figure 3A:
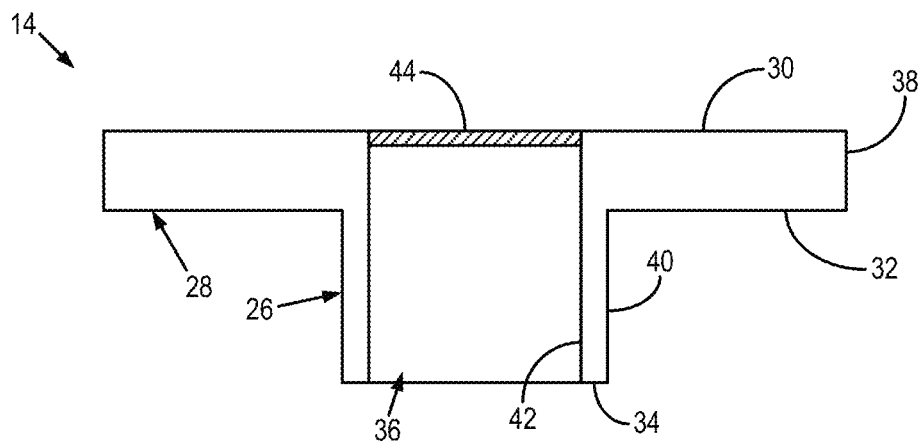
FIGS. 3A-3E show different configurations for a seal arranged within the central lumen of an example medical instrument port according to some embodiments described in the present disclosure.
Figure 3B:
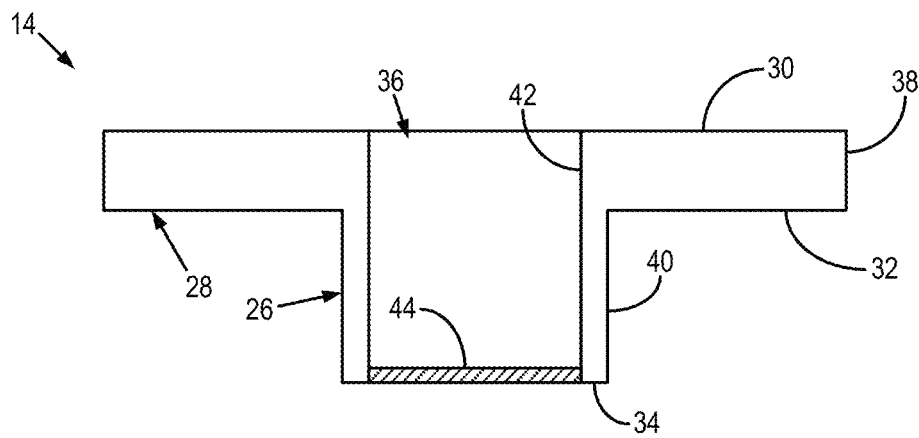
Figure 3C:
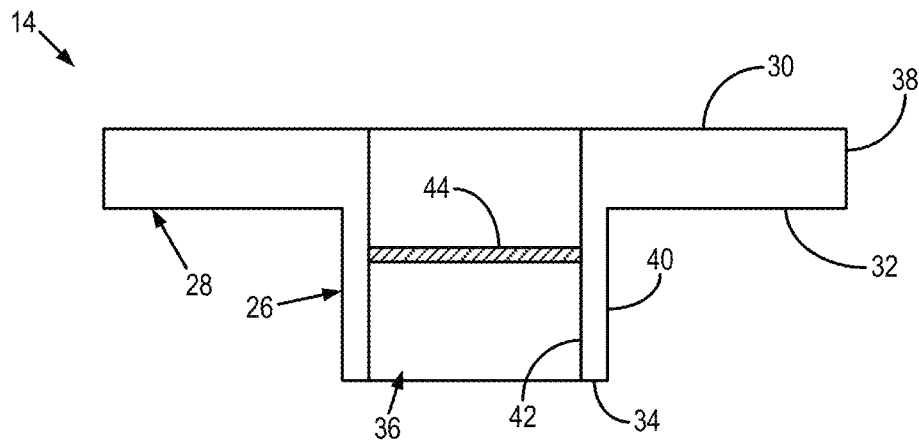

Referring now to FIGS. 3A-3C, a seal 44 is arranged within the central lumen 36 of the second component 14. The seal 44 can generally be constructed as a membrane that spans the central lumen 36. The seal 44 is preferably composed of a flexible material, such as silicone or the like. The seal 44 may be a single uninterrupted membrane, or may include a small pre-formed hole or slit to facilitate passage of a medical instrument through the seal 44. When a medical instrument is passed through the seal 44, the contact between the seal 44 and the medical instrument maintain a barrier to aerosolized droplets, such that the droplets are blocked from passing beyond the seal 44 along the length of the medical instrument, as will be described in more detail below.

As shown in FIG. 3A, the seal 44 can in some instances be arranged within the central lumen 36 near the outward facing surface 30 of the flange 28. Alternatively, as shown in FIG. 3B, the seal 44 can be arranged within the central lumen 36 near the leading edge 34 of the tube 26. As still another example, as shown in FIG. 3C, the seal 44 can be arranged at a point along the length of the central lumen 36 (e.g., a midpoint) that is offset from the outward facing surface 30 of the flange 28 and the leading edge 34 of the tube 26. In still other configurations, two or more seals 44 can be arranged within the central lumen 36 so as to provide increased protection against aerosolized droplets passing through the central lumen 36. As one example, two seals 44 can be arranged within the central lumen 36. The seals 44 may have a cross-slit valve and in some configurations the first seal and the second seal may be rotated relative to each other (e.g., by 45 degrees), such that the flaps of one cross-slit valve will spatially overlap with the openings in the other cross-slit valve, and vice versa. This configuration may provide additional protection against aerosolized droplets from being able to pass through the central lumen 36 when a medical instrument is passed therethrough.

Figure 3D:
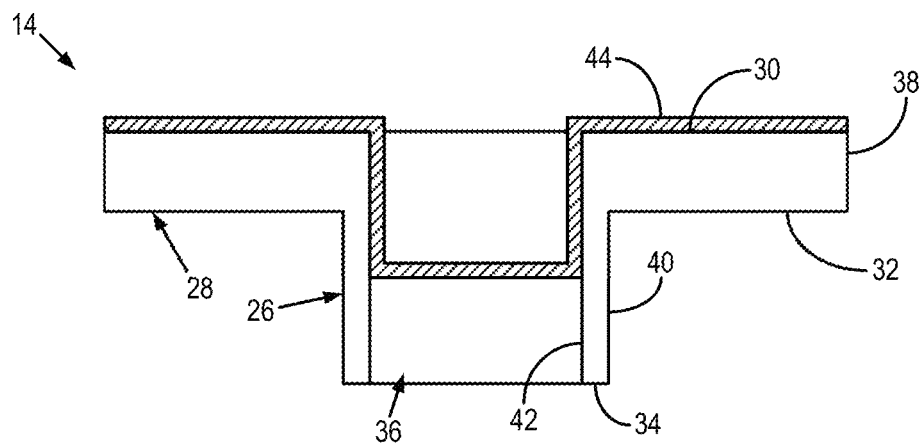
Figure 3E:
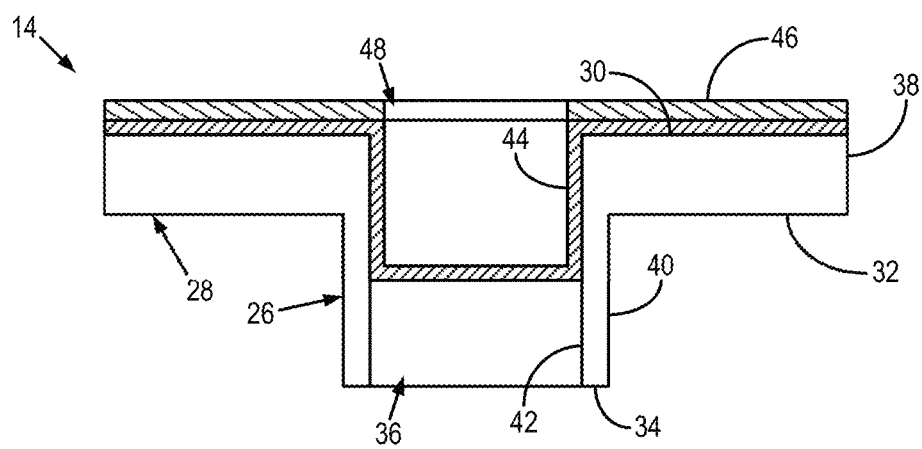

In some instances, the seal 44 can also be provided as a permanent or removable insert that fits within the central lumen 36 of the tube 26, as shown in FIGS. 3D and 3E. For example, the seal 44 can be constructed as a removable sleeve that can be inserted into the central lumen 36 of the tube 26. In such configurations, a portion of the seal 44 is arranged on the outward facing surface 30 of the flange 28 while the other portion of the seal 44 is suspended, inserted, or otherwise extends, into the central lumen 36 of the tube 26. As shown in FIG. 3E, in some configurations a cap 46 can affix or otherwise secure the seal 44 to the outward facing surface 30 of the flange 28. The cap 46 is preferably annular in shape, such that is has a central aperture 48 that is coaxial with the central lumen 36 of the tube 26 when the cap 46 is coupled to the second component 14. As one non-limiting example, the cap 46 can be sized to have a slightly larger diameter than the flange 28 and can have a lip that wholly or partially circumscribes the outer edge 38 of the flange 28, such that the cap 46 can be secured to the second component 14 via an interference fit. As another non-limiting example, the cap 46 can be coupled to the second component 14 via a snap-in connection or the like.

In some configurations, the cap 46 can be a solid cap without a central aperture 48, such that the cap 46 can be coupled to the first component 12 or the second component 14 after a medical instrument has been removed from the medical instrument port 10 (i.e., after the mask has been pierced by the medical instrument) in order to maintain a seal against aerosolized droplets expelled from the patient. The cap 46 may include a ring that is coupled to the cap and sized to fit around an outer periphery of the first component 12 and/or second component 14, such that the cap 46 can remain attached to the first component 12 and/or the second component 14 when not in use. This configuration can advantageously allow for quick access by a clinician during a procedure (e.g., after a medical instrument has been removed from the medical instrument port 10).

Figure 4:
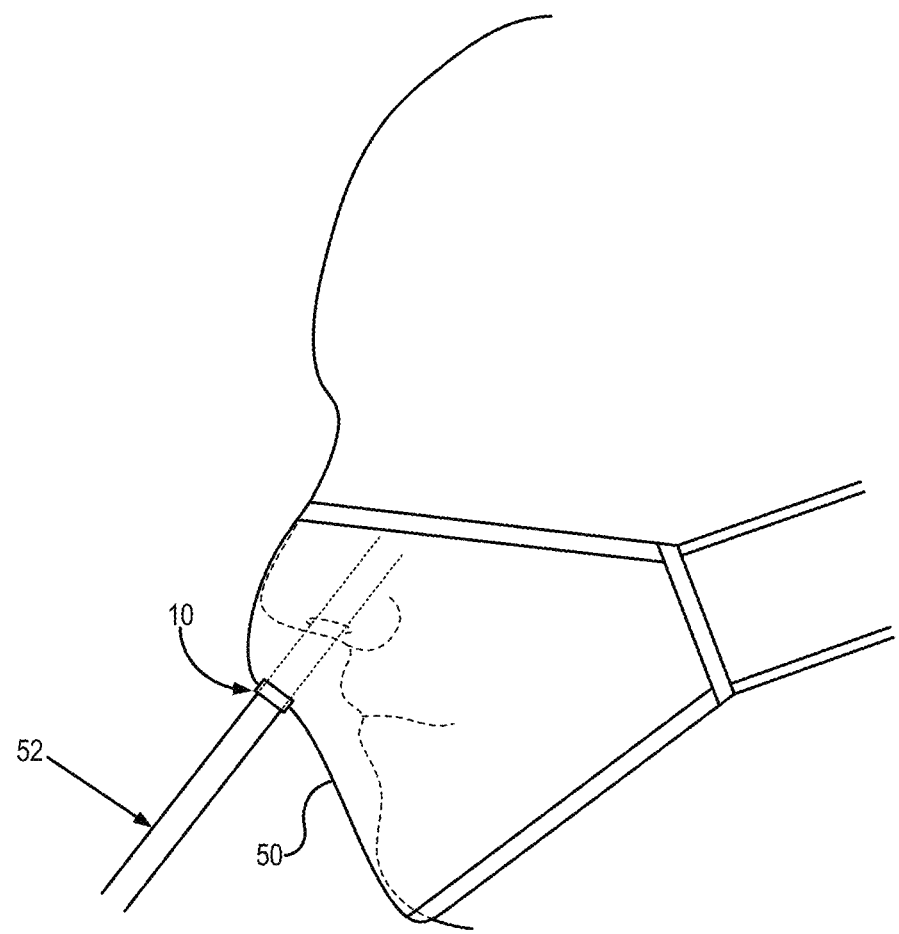
FIG. 4 shows an example medical instrument port affixed to a face mask and in use.
Figure 5:
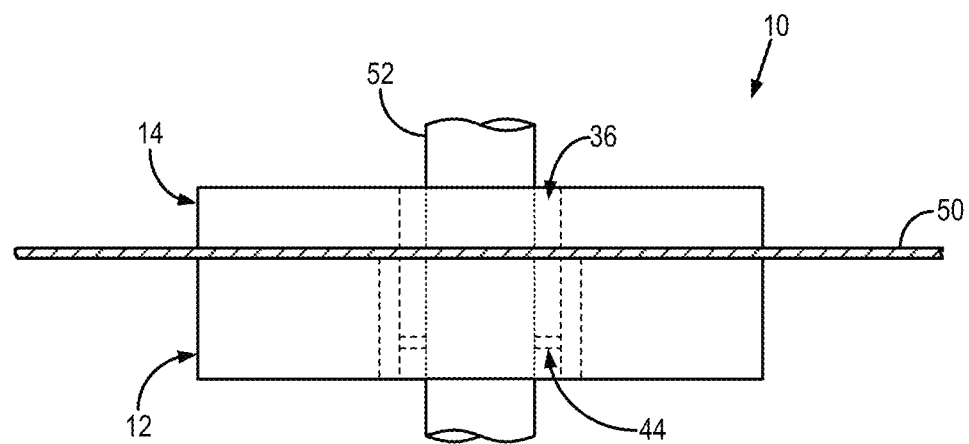
FIG. 5 shows an example medical instrument port affixed to a face mask or other protective covering, through which a medical instrument port has been passed.

As shown in FIGS. 4 and 5, in use, the medical instrument port 10 can be affixed to a face mask 50 by arranging the face mask 50 between the first component 12 and the second component 14 of the medical instrument port 10 and coupling the first component 12 and the second component 14 together. In doing so, the leading edge 34 of the tube 26 will pierce, puncture, or otherwise pass through the face mask 50 before coupling to the first component 12. As a result, the face mask 50 will be pressed between the opposing inward facing surface 18 of the first component 12 and the inward facing surface 32 of the second component 14, maintaining a barrier between the patient and the environment.

A medical instrument 52, such as an endoscope, can then be passed through the channel formed by the central lumen 36 of the second component 14 of the medical instrument port 10. As described above, in some embodiments, the inner diameter of this central lumen 36 is sized to be larger than the outer diameter of the medical instrument 52. The seal 44 is arranged within the channel defined by the central lumen 36 such that when the medical instrument 52 pierces, punctures, or otherwise passes through the seal 44, the medical instrument 52 can be provided to the patient side of the face mask 50 while still providing a barrier between the patient and the environment. In this way, when the medical instrument 52 is introduced into the patient's nasal passage, mouth, or other bodily lumen, any aerosolized droplets expelled from the patient's respiratory system (e.g., by sneezing) will be retained by the face mask 50 and the seal 44 in the medical instrument port 10. As a result, the droplets are prevented from passing along the medical instrument 52 into the surrounding environment.

In some other embodiments, the inner diameter of the central lumen 36 of the second component 14 may be sized such that when the medical instrument 52 is introduced into the medical instrument port 10, a tight seal is formed between the outer surface of the medical instrument 52 and the inner surface 42 of the central lumen 36. As a result, the sealing function of the medical instrument port 10 can be achieved.

In some other configurations, such as those shown in FIGS. 6A-6D, the medical instrument port 10 can include a first component 12 and a second component 14 each having coupled thereto a seal 62. In these configurations, the seal 62 is coupled to a flange 64 that circumscribes or otherwise defines an outer periphery of the first component 12 and/or the second component 14. The seal 62 may be an integral part of the first component 12 and/or second component 14. In other configurations, the seal 62 may be removably coupled to the first component 12 and/or second component 14.

Figure 6A:
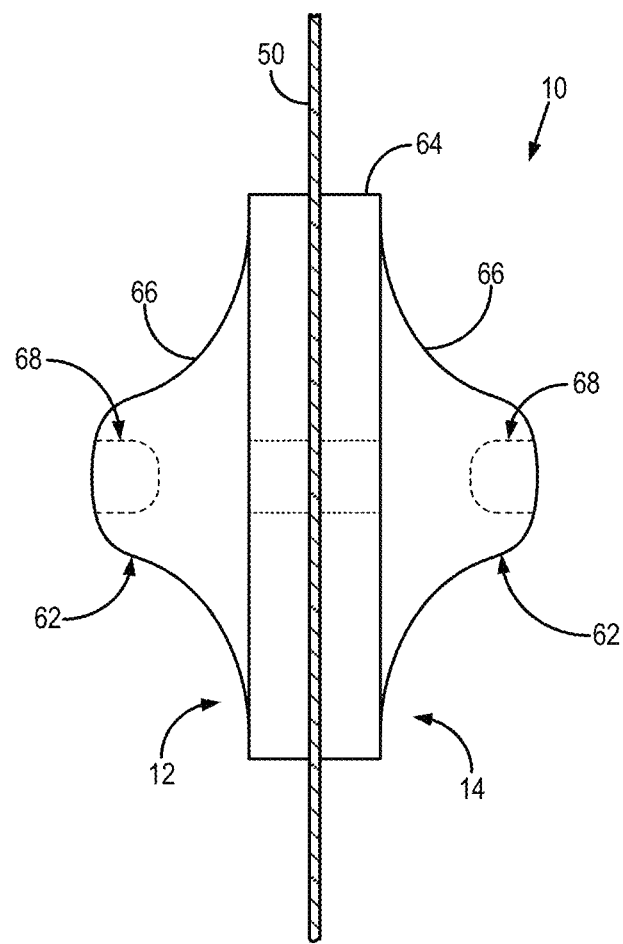
FIG. 6A-6D show alternative configurations of a medical instrument port in which two seals are formed as inverted nipples and/or duckbilled valves.
Figures 6B, 6C:
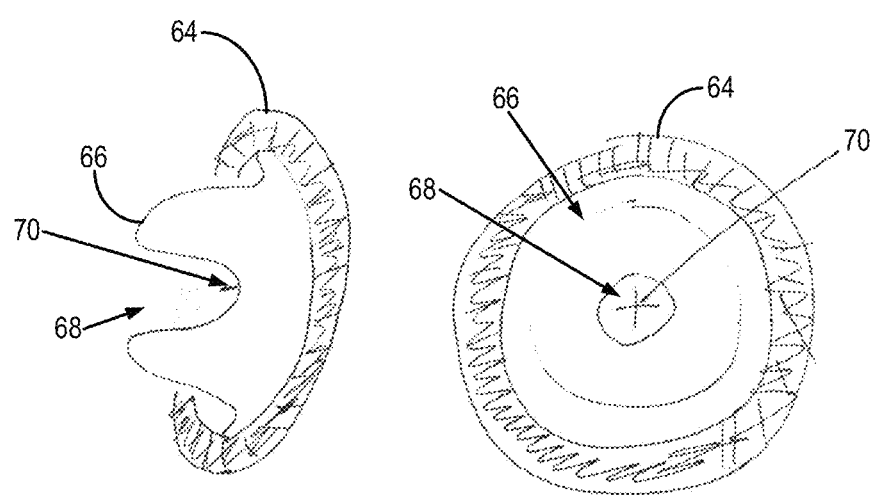

Each seal 62 may include, for instance, a nipple design or an inverted nipple design. For example, as shown in FIGS. 6B and 6C, each seal 62 can include a nipple 66 that is inverted at its tip to form a recess 68. Although the nipple 66 is shown as protruding outward from the outer surfaces of the first component 12 and the second component 14 in FIG. 6A, in an alternative configurations the nipple can be recessed inward from these outer surfaces. A valve 70, which may be formed as a slit, a plurality of slits, an aperture, and so on, is formed in the center of the recess 68 to permit passage a medical instrument therethrough. In some configurations, the valve 70 can form a duckbill valve, a double duckbill valve, or the like.

Figure 6D:
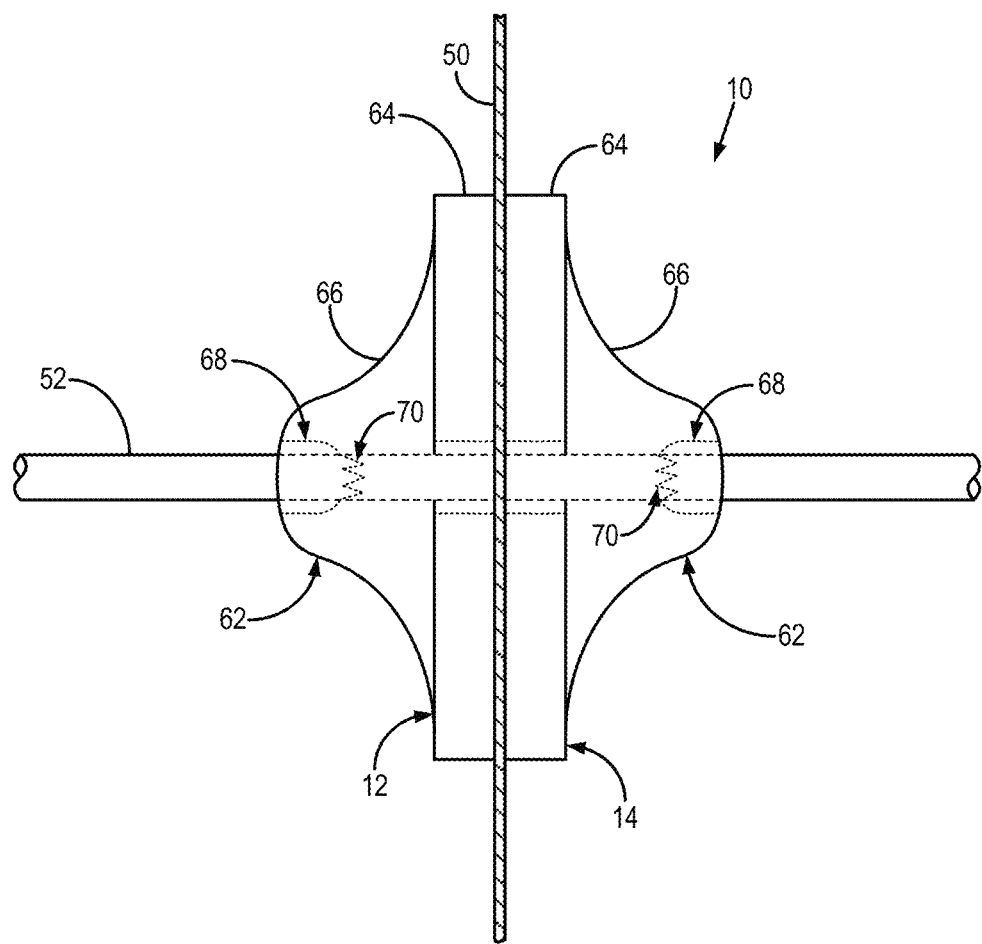

As shown in FIG. 6D, when a medical instrument 52 is inserted through the seal 62 of the first component 12 and the seal 62 of the second component 14 of the medical instrument port 10, the medical instrument will displace the valve 70 away from the medical instrument 52, such as by pushing the flaps of the valve 70 in the first component 12 outward into the inner volume of the first component 12, and pushing the flaps of the valve 70 of the second component 14 outward into the volume on the patient-side of the mask 50. In this way, any aerosolized droplets expelled by the patient will remain on the patient-side of the mask 50. If any aerosolized droplets pass beyond the seal 62 in the second component 14 they will then be trapped in the inner volume between the first component 12 and second component 14 by way of the seal 62 at the first component 12. When the medical instrument 52 is retracted, any aerosolized droplets will be Advantageously, the medical instrument ports described in the present disclosure offer a simple construction, inexpensive manufacturing, and ease of use. For example, the two-component design allows for rapid and simple use of the medical instrument port without requiring additional tools to couple the first and second components of the medical instrument port, or to pierce the face mask or other protective covering when the medical instrument port is in use.

The present disclosure has described one or more preferred embodiments, and it should be appreciated that many equivalents, alternatives, variations, and modifications, aside from those expressly stated, are possible and within the scope of the invention.

The invention claimed is:
1. A medical instrument port, comprising:
a first component having an outer edge and extending from an outward facing surface to an inward facing surface and having formed therein an aperture that extends from the outward facing surface to the inward facing surface;
a second component comprising:
a flange having an outer edge and extending from an outward facing surface to an inward facing surface; and
a tube coupled to the flange and extending from the inward facing surface of the flange to a leading edge of the tube;
wherein a central lumen is formed in the second component, which extends from the outward facing surface of the flange to the leading edge of the tube;
wherein the aperture formed in the first component is sized to receive the tube of the second component such that when in a coupled state the first component and the second component define a port through which a medical instrument can pass;
wherein the flange is sized such that a distance between an outer surface of the tube and an outer edge of the flange defines a surface area on the inward facing surface of the flange sufficient to retain a face mask between the inward facing surface of the first component and the inward facing surface of the flange when in the coupled state;
wherein the first component is coupled to the second component in the coupled state via an interference fit between the tube and the aperture;
wherein when in the coupled state an interface where the outer edge of the first component meets the outer edge of the flange is exposed to permit retention of the face mask between the inward facing surface of the first component and the inward facing surface of the flange.

2. The medical instrument port of claim 1, further comprising a seal that spans the central lumen of the second component.

3. The medical instrument port of claim 2, wherein the seal comprises a flexible membrane.

4. The medical instrument port of claim 3, wherein the flexible membrane is composed of silicone.

5. The medical instrument port of claim 2, wherein the seal is arranged within the central lumen adjacent the outward facing surface of the flange.

6. The medical instrument port of claim 2, wherein the seal is arranged within the central lumen adjacent the leading edge of the tube.

7. The medical instrument port of claim 1, further comprising a seal having a sleeve portion, wherein the seal is coupled to the second component such that the sleeve portion of the seal is arranged within the central lumen.

8. The medical instrument port of claim 7, wherein the seal further comprises a flange portion in contact the outward facing surface of the flange of the second component when the seal is coupled to the second component.

9. The medical instrument port of claim 8, further comprising a cap coupled to the second component such that the flange portion of the seal is arranged between the cap and the outward facing surface of the flange of the second component.

10. The medical instrument port of claim 1, wherein the tube is integrally formed with the flange.

11. The medical instrument port of claim 1, wherein the leading edge of the tube is angled with respect to the inward facing surface of the flange, thereby defining a cutting edge.

12. The medical instrument port of claim 1, wherein the first component has a circular annular shape.

13. The medical instrument port of claim 1, wherein the flange has a circular annular shape and the tube is a cylindrical tube.

14. The medical instrument port of claim 1, wherein the tube has a length such that when the first component and the second component are in the coupled state the length of the tube does not extend beyond the outward facing surface of the first component.

15. The medical instrument port of claim 1, wherein the central lumen has an inner diameter less than 12 mm.

16. The medical instrument port of claim 15, wherein the inner diameter of the central lumen is between 2 and 4 mm.

17. The medical instrument port of claim 1, further comprising:
   a first seal coupled to the first component and spanning the aperture; and
   a second seal coupled to the second component and spanning the central lumen.

18. The medical instrument port of claim 17, wherein the first seal and the second seal each comprise a duckbill valve.

19. The medical instrument port of claim 17, wherein the first seal and the second seal each comprise an inverted nipple.

20. The medical instrument port of claim 17, wherein the first seal and the second seal each comprise a cross-slit valve.

21. The medical instrument port of claim 20, wherein the first seal is rotationally offset from the second seal about a longitudinal axis passing through the aperture and the central lumen.

* * * * *